United States Patent
Nishino et al.

(10) Patent No.: US 7,524,952 B2
(45) Date of Patent: Apr. 28, 2009

(54) PROCESS FOR PRODUCING CARBAPENEM COMPOUND FOR ORAL ADMINISTRATION

(75) Inventors: Keita Nishino, Hyogo (JP); Teruyoshi Koga, Hyogo (JP)

(73) Assignee: Kaneka Corporation, Osaka (JP)

( * ) Notice: Subject to any disclaimer, the term of this patent is extended or adjusted under 35 U.S.C. 154(b) by 377 days.

(21) Appl. No.: 10/533,183

(22) PCT Filed: Nov. 13, 2003

(86) PCT No.: PCT/JP03/14420

§ 371 (c)(1),
(2), (4) Date: Apr. 28, 2005

(87) PCT Pub. No.: WO2004/043961

PCT Pub. Date: May 27, 2004

(65) Prior Publication Data

US 2006/0009442 A1 Jan. 12, 2006

(30) Foreign Application Priority Data

Nov. 13, 2002 (JP) .............................. 2002-330128

(51) Int. Cl.
*C07D 477/06* (2006.01)
*C07D 477/20* (2006.01)
*C07D 477/04* (2006.01)

(52) U.S. Cl. ...................... 540/350; 540/200

(58) Field of Classification Search ................ 540/350
See application file for complete search history.

(56) References Cited

U.S. PATENT DOCUMENTS

| 5,414,081 A * | 5/1995 | Horikawa et al. ........... 540/302 |
| 5,424,422 A | 6/1995 | Sunagawa et al. | |
| 5,578,722 A * | 11/1996 | Sunagawa et al. ........... 540/302 |
| 2007/0244089 A1* | 10/2007 | Kim et al. ............... 514/210.12 |

FOREIGN PATENT DOCUMENTS

| EP | 0188816 A1 | 7/1986 |
| EP | 0 559 533 A1 | 9/1993 |
| EP | 0 632 039 A1 | 1/1995 |
| JP | 62-103084 | 5/1987 |
| JP | 10-130270 A | 5/1998 |
| WO | WO 2004/035539 A1 | 4/2004 |

OTHER PUBLICATIONS

Sakurai, J. Org. Chem 61, 7889 (1996).*

Theodora W. Greene, Peter G. M. Wuts, Protective Groups in Organic Synthesis (Third Edition) 1999, pp. 127-141.*

International Search Report from Corresponding International Application No. PCT/JP03/14420, dated Feb. 24, 2004, 2 pages.

* cited by examiner

*Primary Examiner*—Mark L Berch
(74) *Attorney, Agent, or Firm*—Brinks Hofer Gilson & Lione

(57) ABSTRACT

The present invention provides a process for efficiently producing a 1β-methylcarbapenem compound for oral administration. The process, which is for producing a 1β-methylcarbapenem compound represented by general formula (2), is characterized by reacting a β-lactam compound represented by general formula (1) as a starting material with a thiol compound ($R_3$—SH) in the presence of a base and optionally eliminating the protective group $R_1$.

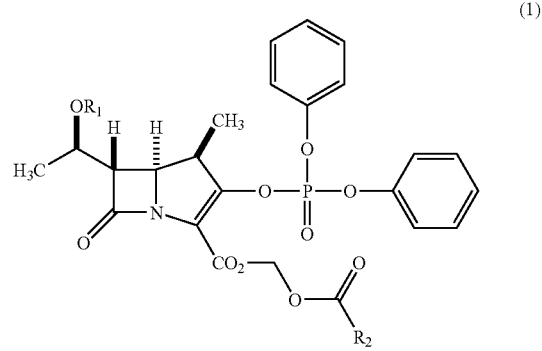

(1)

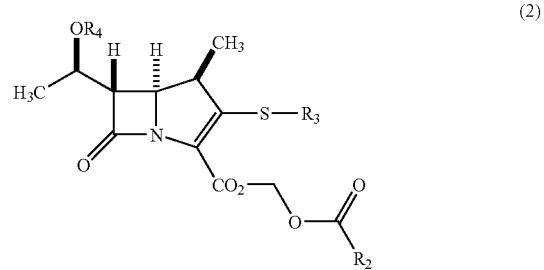

(2)

In the formulae (1) and (2), $R_1$ denotes a hydrogen atom, a trimethylsilyl group or a triethylsilyl group; $R_2$ denotes an alkyl group having 1 to 10 carbon atoms or a cycloalkyl group having 3 to 10 carbon atoms; $R_3$ denotes an organic group; and $R_4$ denotes hydrogen, a trimethylsilyl group or a triethylsilyl group.

3 Claims, No Drawings

PROCESS FOR PRODUCING CARBAPENEM COMPOUND FOR ORAL ADMINISTRATION

RELATED APPLICATIONS

This application is a nationalization of PCT Application No. PCT/JP2003/014420 filed Nov. 13, 2003. This application claims priority from Japanese Patent Application No. 2002-330128 filed on Nov. 13, 2002.

TECHNICAL FIELD

The present invention relates to an efficient and extremely useful process for producing a 1 β-methylcarbapenem compound for oral administration.

BACKGROUND ART

A 1β-methylcarbapenem compound is one of the antibacterial agents attracting the most attention because it shows an excellent antibacterial effect on a wide variety of pathogenic organisms and is excellent in stability in vivo. Accordingly, various research and development have been made energetically in recent years attempting to produce the drugs for oral administration. Processes for producing a 1β-methylcarbapenem compound for oral administration, which are generally used at present, include the following processes.

For example, there is described a process in Japanese Unexamined Patent Application Publication No. 8-53453 and J. Antibiot., p. 429-439, 1997, which comprises the steps of reacting a compound represented by formula (6):

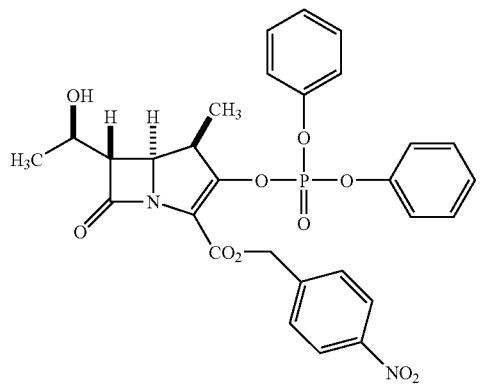

(6)

with each of various thiol compounds (R—SH) to synthesize a compound represented by formula (7):

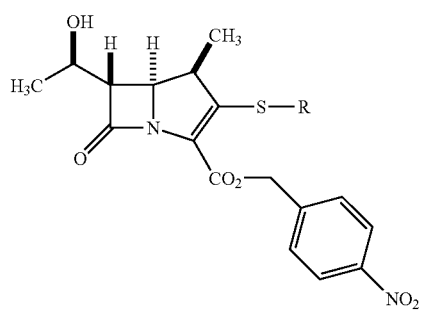

(7)

wherein R denotes a thiol residue; eliminating a p-nitrobenzyl group, a protective group, from the compound represented by formula (7), for example, by hydrogenolysis or reduction by a zinc powder to convert it to a compound represented by formula (8):

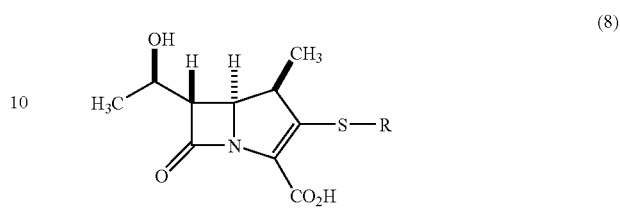

(8)

wherein R denotes a thiol residue; and subjecting the carboxylic moiety of the resulting compound (8) to pivaloyloxymethylation to produce a compound represented by formula (9):

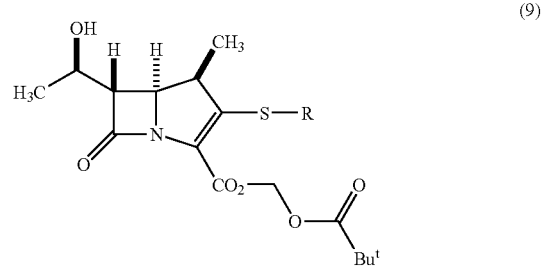

(9)

wherein R denotes a thiol residue, and $Bu^t$ denotes a tert-butyl group.

As the compounds represented by formula (9), for example, in Japanese Unexamined Patent Application Publication Nos. 8-53453 and 10-195076 is described a compound represented by formula (10):

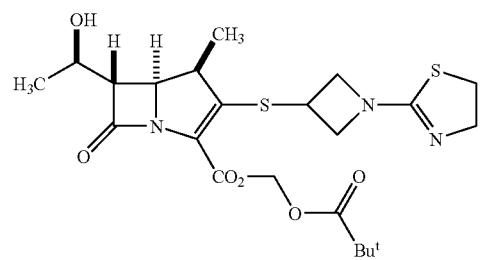

(10)

; in J. Antibiot., P. 429-439, 1997 and Japanese Unexamined Patent Application Publication No. 10-130270 is described a compound represented by formula (11):

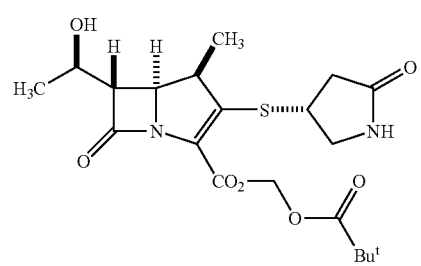

(11)

; and in Japanese Unexamined Patent Application Publication No. 10-152491 is described a compound represented by formula (12):

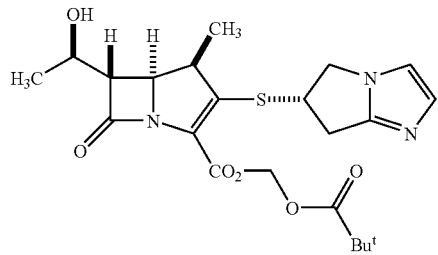

(12)

All of these compounds are synthesized by the above-described process.

However, when 1β-methylcarbapenem compound for oral administration is produced by these production processes, it is necessary to exchange the protecting group of carboxylic acid through multistep reactions, which is ineffective; and relatively expensive thiol compounds, each of which is related to a thiol residue in a final product, are used in the initial stage of synthesis, which is disadvantageous in terms of production cost. These have been regarded as problems in the above production processes.

Furthermore, in Japanese Unexamined Patent Application Publication Nos. 8-59663 and 2000-344774 is described a process for producing a compound represented by formula (15):

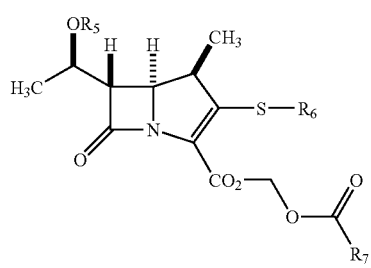

(15)

wherein $R_5$ denotes a hydroxy-protecting group; $R_6$ denotes a thiol residue contained in a 1β-methylcarbapenem compound, a product; and $R_7$ denotes an organic group, by the steps of synthesizing a compound represented by formula (14):

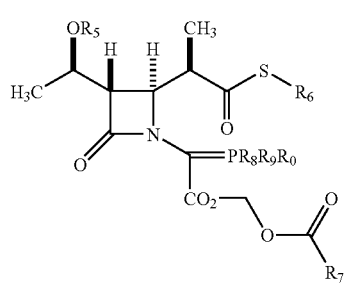

(14)

wherein $R_5$, $R_6$ and $R_7$ each denote the same as described above; and $R_8$, $R_9$ and $R_0$ each denote a lower alkoxy group having 1 to 4 carbon atoms, or any one of $R_8$, $R_g$ and $R_0$ denotes an alkyl group having 1 to 4 carbon atoms and remaining two each denote a lower alkoxy group having 1 to 4 carbon atoms, from a compound represented by formula (13):

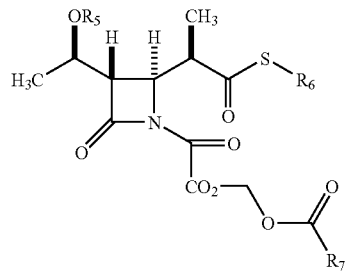

(13)

wherein $R_5$, $R_6$ and $R_7$ each denote the same as described above, and cyclizing the compound represented by formula (14).

However, in this production process also, relatively expensive thiol compounds, each of which is related to a thiol residue in a final product, are used in the initial stage of synthesis in the same manner as described above. Therefore, the process is also disadvantageous in terms of production cost, which has been regarded as a problem.

Furthermore, in J. Org. Chem., vol. 61, P. 7889-7894, 1996 and Japanese Unexamined Patent Application Publication No. 5-279367 is described a compound represented by formula (16):

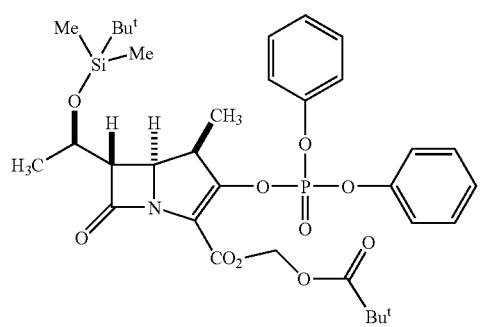

(16)

wherein Me denotes a methyl group; and $Bu^t$ denotes the same as described above. It may be considered that the compound is converted to a 1β-methylcarbapenem compound by allowing it to react with any of various thiol compounds and by deprotection of a hydroxy group. However, since a tert-butyldimethylsilyl group is used as the hydroxy-protecting group in the above compound (16), it is necessary to use a reagent that influences other functional groups in order to perform deprotection at the hydroxylic moiety, as illustrated in Protective Groups in Organic Synthesis (J Wiley & Sons, New York), P. 44-46, 1981. This is a problem in terms of yields or the like. The present inventors have made various studies on the method of deprotection, and have found that it is difficult to perform deprotection easily and efficiently.

Under the circumstances as described above, the development of a efficient process for producing a 1β-methylcarbapenem compound for oral administration, wherein the process is advantageous in terms of production cost, has been desired.

SUMMARY OF THE INVENTION

In view of the above circumstances, the present inventors have extensively studied on the development of a production process in which a thiol compound can be introduced by one step at the final stage of the synthesis of a 1β-methylcarbapenem compound for oral administration. As a result of the extensive study, the present invention has been accomplished.

Specifically, the present invention provides a process for producing a compound represented by general formula (2)

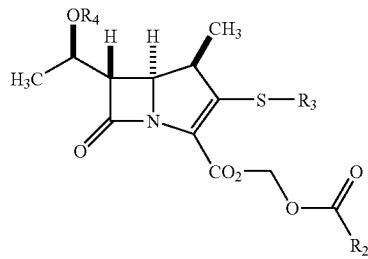
(2)

wherein $R_2$ denotes an alkyl group having 1 to 10 carbon atoms or a cycloalkyl group having 3 to 10 carbon atoms; $R_3$ denotes an organic group; and $R_4$ denotes a hydrogen atom, a trimethylsilyl group or a triethylsilyl group, characterized by reacting a compound represented by general formula (1):

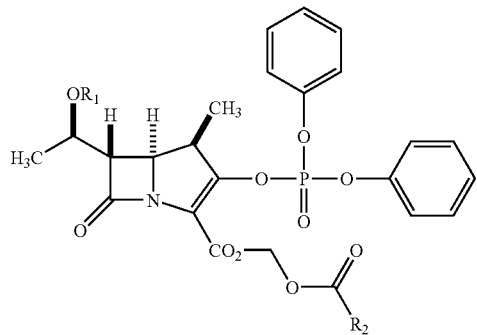
(1)

wherein $R_1$ denotes a hydrogen atom, a trimethylsilyl group or a triethylsilyl group; $R_2$ denotes the same as described above, with a thiol compound represented by general formula (3):

$$R_3\text{—SH} \quad (3)$$

wherein $R_3$ denotes the same as described above, in the presence of a base and optionally eliminating the protective group $R_1$.

DETAILED DISCLOSURE OF THE INVENTION

The present invention will now be described in detail below.

The present invention provides a process for producing a compound represented by general formula (2):

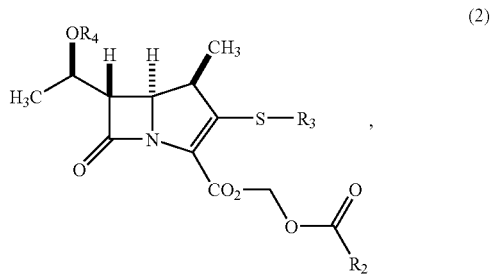
(2)

characterized by reacting a compound represented by general formula (1):

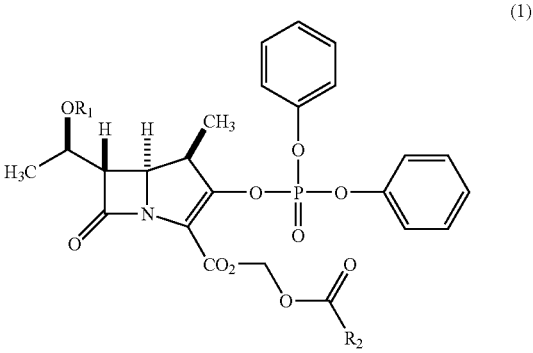
(1)

with a thiol compound represented by general formula (3):

$$R_3\text{—SH} \quad (3)$$

in the presence of a base and optionally eliminating the protective group $R_1$.

Substituents in each compound will first be described. The substituent $R_1$ denotes a hydrogen atom, a trimethylsilyl group or a triethylsilyl group. When the substituent $R_1$ is a hydrogen atom, there is obtained a compound (2) in which the substituent $R_4$ is a hydrogen atom. On the other hand, from the compound (1) in which the substituent $R_1$ is a trimethylsilyl group or a triethylsilyl group, there is produced a compound (2) in which the substituent $R_4$ is a trimethylsilyl group or a triethylsilyl group. In this case, the compound (2) having the substituent $R_4$ which is obtained as a product is different from the conventionally known compound represented by (16) as described above in that it can easily deprotect the hydroxy group to obtain the compound (2) having a hydrogen atom as the substituent $R_4$. The substituent $R_1$ is selected such that, when the compound (2) obtained as a product is subjected to deprotection reaction, it can be eliminated under a mild condition with minimum decomposition of other functional group moieties in the compound to the extent possible. In order to facilitate the deprotection, when the substituent $R_1$ is a hydroxy-protecting group, it needs to be a trimethylsilyl group or a triethylsilyl group, preferably a trimethylsilyl group.

The substituent $R_2$ denotes an alkyl group having 1 to 10 carbon atoms or a cycloalkyl group having 3 to 10 carbon atoms, which may be contained in the alkanoyloxymethyl group portion of a carboxylate residue in a compound that may finally be developed as a 1β-methylcarbapenem compound for oral administration.

Examples of the alkyl group having 1 to 10 carbon atoms include methyl, ethyl, n-propyl, iso-propyl, n-butyl, iso-butyl, sec-butyl, tert-butyl, n-octyl, n-decanyl and the like.

The cycloalkyl group having carbon atoms of 3 to 10 may have a substituent, which includes an alkyl group having carbon atoms of 1 to 4 such as methyl and ethyl, and the like. Examples of the cycloalkyl group having carbon atoms of 3 to 10 include cyclopropyl, cyclohexyl, 1-methylcyclohexyl, 4-methylcyclohexyl and the like.

As the substituent $R_2$, a tert-butyl group, which is often used in the development of a carbapenem compound for oral administration, is most preferred among others.

The substituent $R_3$ denotes an organic group, which may preferably be contained in the thiol residue in a compound that may finally be developed as a 1β-methylcarbapenem compound for oral administration. More preferably, examples of the thiol residue of a thiol compound represented by general formula (3):

(wherein $R_3$ denotes an organic group) include the thiol residue of a compound which is described in Japanese Unexamined Patent Application Publication No. 8-53453, represented by formula (4):

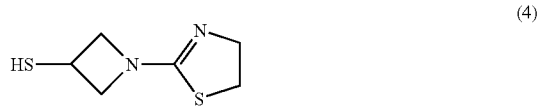

; the thiol residue of a compound which is described in J. Antibiot., P. 429-439, 1997, represented by formula (5):

; and the thiol residue of a compound which is described in Japanese Unexamined Patent Application Publication No. 10-152491, represented by formula (19):

The substituent $R_3$ is preferably the thiol residue of a compound represented by formula (4) or the thiol residue of a compound represented by formula (5).

The substituent $R_4$ denotes a hydrogen atom, a trimethylsilyl group or a triethylsilyl group. As described above, when the substituent $R_4$ is a trimethylsilyl group or a triethylsilyl group, a 1β-methylcarbapenem compound for oral administration can be easily obtained by eliminating it as necessary.

A production process of the present invention will now be described.

The compound represented by formula (1), which is the starting raw material to be used in the present invention, can be derived from a compound represented by formula (17):

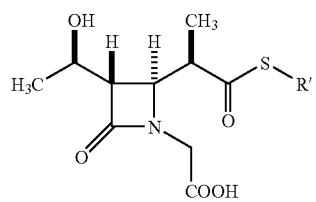

wherein R' denotes an aryl group or a heterbaryl group, which may have a substituent, examples of which are described in detail as reference examples 1 to 4. The compound represented by formula (17) can be easily prepared according to the description in Chem. Pharm. Bull., vol. 42, P. 1381-1387, 1994.

The compound (1) is reacted with the thiol compound represented by formula (3) in the presence of a base to obtain a 1β-methylcarbapenem compound represented by formula (2).

The reaction is performed in an inert solvent which does not decompose the compound (1). Examples of the inert solvent include, but not limited to, ether solvents such as tetrahydrofuran, dioxane and diethyl ether; aromatic hydrocarbon solvents such as benzene, toluene and xylene; amide solvents such as N,N-dimethylformamide and N,N-dimethylacetamide; dimethyl sulfoxide, acetonitrile, acetone, methylene chloride and mixed solvents thereof, and the like. Most preferred are N,N-dimethylformamide, N,N-dimethylacetamide and acetonitrile, in terms of reaction rate.

The molar amount of the thiol compound (3) to be used in the reaction needs to be 1.0 time or more as compared to that of the compound (1), preferably from 1.1 to 3.0 times. The thiol compound (3) may form a salt such as a hydrochloride.

Furthermore, the base to be used may include organic amines, alkali metal salts, alkali metal alkoxides, alkali metal amides, alkali metal hydrides and the like.

Examples of the organic amines include triethylamine, diisopropylethylamine, 4-dimethylaminopyridine, 1,8-diazabicyclo[5.4.0]-undec-7-ene (DBU), 1,5-diazabicyclo[4.3.0]-non-5-ene (DBN), and 1,4-diazabicyclo[2.2.2] octane (DABCO). When organic amines are used, the molar amount of the same to be used needs to be 1.0 time or more as compared to that of the compound (1), preferably from 1.1 to 3.0 times.

Examples of the alkali metal salts include alkali metal carbonates such as sodium carbonate, potassium carbonate and cesium carbonate; alkali metal bicarbonates such as sodium bicarbonate and potassium bicarbonate; and the like. When the alkali metal carbonates are used, the molar amount of the same to be used needs to be 0.5 time or more as compared to that of the compound (1), preferably from 1.1 to 2.0 times. When the alkali metal bicarbonates are used, the molar amount of the same to be used needs to be 1.0 time or more as compared to that of the compound (1), preferably from 1.1 to 2.0 times.

Examples of the alkali metal alkoxides include potassium tert-butoxide, sodium tert-butoxide and the like. When the alkali metal alkoxides are used, the molar amount of the same to be used needs to be 1.0 time or more as compared to that of the compound (1), preferably 1.1 to 2.0 times.

Examples of the alkali metal amides include lithium bis (trimethylsilyl)amide, sodium bis (trimethylsilyl)amide, potassium bis(trimethylsilyl)amide and the like. When the alkali metal amides are used, the molar amount of the same to be used needs to be 1.0 time or more as compared to that of the compound (1), preferably 1.1 to 2.0 times.

Examples of the alkali metal hydrides include sodium hydride, potassium hydride and the like. When the alkali metal hydrides are used, the molar amount of the same to be used needs to be 1.0 time or more as compared to that of the compound (1), preferably 1.1 to 2.0 times.

The above reaction is performed typically in the range of −78° C. to 60° C., preferably in the range of −40° C. to 40° C. in order to inhibit decomposition of the reactants and products.

Furthermore, the reaction time is typically in the range of 5 minutes to 40 hours, preferably in the range of one hour to 30 hours from the above reason.

Naturally, the progress of the reaction with time can be obtained by analytic means such as thin layer chromatography (TLC) and high-performance liquid chromatography (HPLC).

The target compound (2) can be isolated from the mixture after the reaction through operations such as pH-adjustment, extraction, liquid separation, washing, concentration, purification and the like, which are frequently used in typical organic reactions.

When the substituent $R_1$ of the compound (1) is a hydrogen atom, the compound (2) having a hydrogen atom as the substituent $R_4$ can be obtained in the above reaction. Thus, a 1β-methylcarbapenem compound for oral administration can be directly obtained.

On the other hand, when the substituent $R_1$ is a trimethylsilyl group or a triethylsilyl group, the resulting compound (2) has a trimethylsilyl group or a triethylsilyl group as the substituent $R_4$, respectively. The above hydroxy-protecting group (a trimethylsilyl group or a triethylsilyl group) as the substituent $R_1$ is selected as a substituent which can be easily eliminated. Accordingly, when pH of the mixture after the reaction is adjusted in the operation such as extraction, washing or the like, the deprotection of the hydroxylic moiety can be performed at the same time as the operation by creating an acidic condition in the mixture. Thus, the compound (2) having a trimethylsilyl group or a triethylsilyl group as the substituent $R_4$ can be easily converted to the compound (2) having a hydrogen atom as the substituent $R_4$, thereby obtaining a 1β-methylcarbapenem compound for oral administration.

The acidic condition to be used in the above operation is not particularly limited as long as the pH is 7 or less, and the pH is preferably in the range of 2 to 6. In this pH range, the hydroxy-protecting group can be eliminated extremely easily. In order to achieve the above acidic condition, for example, an aqueous citric acid solution, hydrochloric acid or the like can be added to the extract or the like.

Furthermore, when the substituent $R_4$ is a trimethylsilyl group or a triethylsilyl group, the compound (2) may be once isolated from the reaction mixture to eliminate it separately. In addition to the above-described method, typical conditions for eliminating silyl protecting groups, as described, for example, in "Protective Groups in Organic Synthesis" (J Wiley & Sons, New York), pp. 39-50, 1981, can be adopted as the deprotection method in this case.

A 1β-methylcarbapenem compound represented by formula (2) can be synthesized efficiently and easily in short steps from a compound represented by formula (1) and a thiol compound represented by formula (3) according to the present invention. The present invention provides a preferable process as a process in which a thiol compound represented by formula (4) or (5) is particularly used as the thiol compound represented by formula (3) to synthesize a 1β-methylcarbapenem compound for oral administration represented by formula (10):

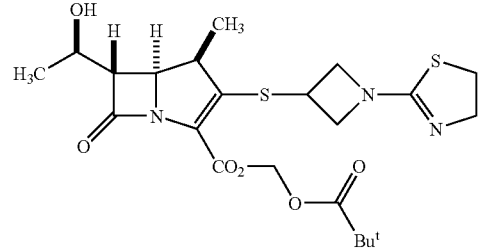

wherein $Bu^t$ denotes a tert-butyl group, or by formula (11):

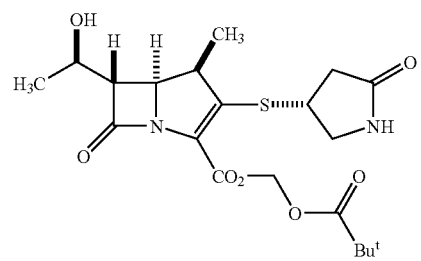

wherein $Bu^t$ denotes the same as above, respectively.

BEST MODE FOR CARRYING OUT THE INVENTION

The present invention will now be described in more detail below with reference to examples and reference examples, but is not particularly limited at all to these descriptions. The meaning of the abbreviations used in the following examples and reference examples is as follows:

Me: methyl group $Bu^t$: tert-butyl group

TMS: trimethylsilyl group

TES: triethylsilyl group

REFERENCE EXAMPLE 1

Production of (3S,4S)-4-[(1R)-1-(p-chlorophenylthiocarbonyl)ethyl]-3-[(1R)-1-hydroxyethyl]-1-pivaloyloxymethyloxycarbonylmethyl-2-azetidinone

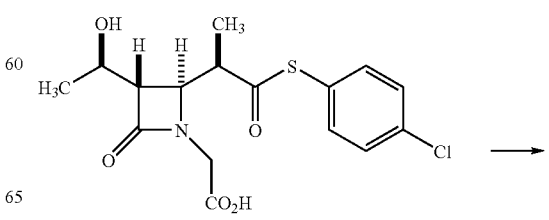

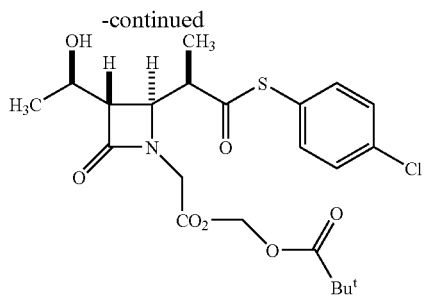

In 18 ml of dimethylformamide, was dissolved 8.18 g (22.0 mmol) of (3S,4S)-1-carboxymethyl-4-[(1R)-1-(p-chlorophenylthiocarbonyl)ethyl]-3-[(1R)-1-hydroxyethyl]-2-azetidinone at room temperature. To the resulting solution, were successively added 5.5 ml (40.0 mmol) of pivaloyloxymethyl chloride and 5.75 g (40.3 mmol) of sodium iodide, and was added dropwise 4.2 ml (25.3 mmol) of diisopropylethylamine, followed by stirring the mixture for 20 hours at the same temperature. The reaction mixture was diluted with 120 ml of toluene. The toluene solution was washed with 2.5% aqueous sodium bicarbonate solution and water, each several times. The resulting toluene solution was dried over sodium sulfate, and then the solvent was removed by evaporation. The resulting oily residue was dissolved in 60 ml of toluene at room temperature. To the resulting solution was added 120 ml of hexane, precipitating a crystal, which was filtered and washed to obtain 9.46 g of a white crystal of the title compound (yield: 92.7%).

NMRδ (CDCl$_3$): 1.19 (9H, s), 1.32-1.34 (6H, m), 3.11-3.18 (2H, m), 3.87 (1H, d, J=18.1 Hz), 4.15 (1H, dd, J=2.4, 4.4 Hz), 4.22-4.24 (1H, m), 4.35 (1H, d, J=18.1 Hz), 5.76 (2H, s), 7.31 (2H, d, J=8.8 Hz), 7.40 (2H, d, J=8.8 Hz)

REFERENCE EXAMPLE 2

Production of (4R,5R,6S)-6-[(1R)-1-trimethylsilyloxyethyl]-3-diphenylph osphoryloxy-4-methyl-7-oxo-1-azabicyclo[3.2.0]hept-2-ene-2-carboxylic acid pivaloyloxymethyl ester

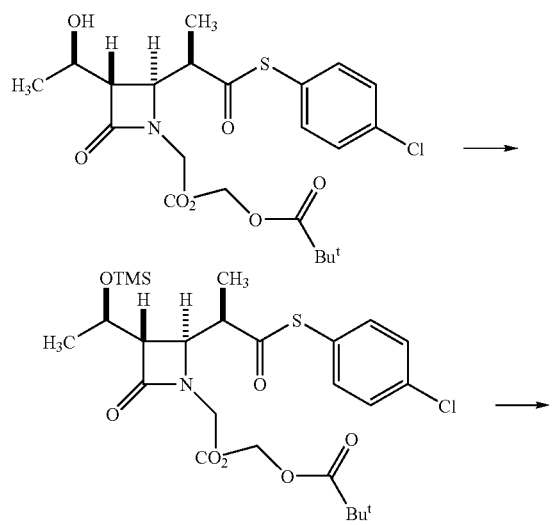

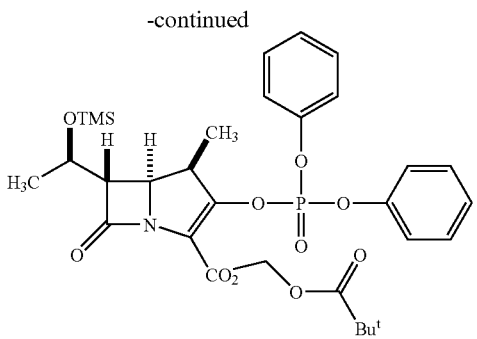

In 20 ml of toluene, was dissolved 1.997 g (4.1 mmol) of (3S,4S)-4-[(1R)-1-(p-chlorophenylthiocarbonyl)ethyl]-3-[(1R)-1-hydroxyethyl]-1-pivaloyloxymethyloxycarbonylmethyl-2-azetidinone which was synthesized in the same manner as in Reference Example 1. To the resulting solution, was added 0.88 mL (6.4 mmol) of triethylamine and was dropwise added 0.78 mL (6.2 mmol) of trimethylsilyl chloride at room temperature, followed by stirring the mixture for 15 hours at the same temperature. The reaction mixture was diluted with 5 ml of toluene. The toluene solution was washed with water several times. The resulting toluene solution was dried over sodium sulfate, and then the solvent was removed by evaporation.

To 2.63 g of the resulting oily residue, was added 22.5 ml of tetrahydrofuran to dissolve the oily residue. The solution was cooled to −70° C., and 0.956 g (8.5 mmol) of potassium tert-butoxide was added to the cooled solution, followed by stirring the mixture for 15 minutes. Then, 0.26 mL (4.2 mmol) of methyl iodide was added to the mixture at the same temperature. The resulting mixture was stirred for 25 minutes while gradually raising the temperature to −35° C., followed by adding 1.0 mL (4.9 mmol) of diphenylphosphoryl chloride to the mixture at −35° C. The resulting mixture was stirred for 1.8 hours while gradually raising the temperature to −9° C. The reaction mixture was diluted with 20 ml of toluene. The toluene solution was washed with 2.5% aqueous sodium bicarbonate solution and water, each several times under cooling with ice. The resulting toluene solution was dried over sodium sulfate, and then the solvent was removed by evaporation to obtain the title compound.

High-performance liquid chromatography was used as the means for tracking the progress of the reaction for the purpose of analysis. The reaction mixture and the titled compound obtained were analyzed by dissolving them in an eluant which was prepared by mixing acetonitrile/water/phosphoric acid in a ratio of 700/300/1. As a result, a compound was detected at the same retention time as that of the product to be described in Reference Example 3. This revealed that the trimethylsilyl group as a hydroxy-protecting group was easily eliminated.

NMRδ (CDCl$_3$): 0.11 (9H, s), 1.19-1.29 (15H, m), 3.24 (1H, dd, J=2.9, 6.6 Hz), 3.45-3.50 (1H, m), 4.07-4.19 (2H, m), 5.78 (1H, d, J=5.5 Hz), 5.81 (1H, d, J=5.5 Hz), 7.15-7.40 (12H, m)

REFERENCE EXAMPLE 3

Production of (4R,5R,6S)-6-[(1R)-1-hydroxyethyl]-3-diphenylphosphorylox y-4-methyl-7-oxo-1-azabicyclo[3.2.0]hept-2-ene-2-carboxylic acid pivaloyloxymethyl ester

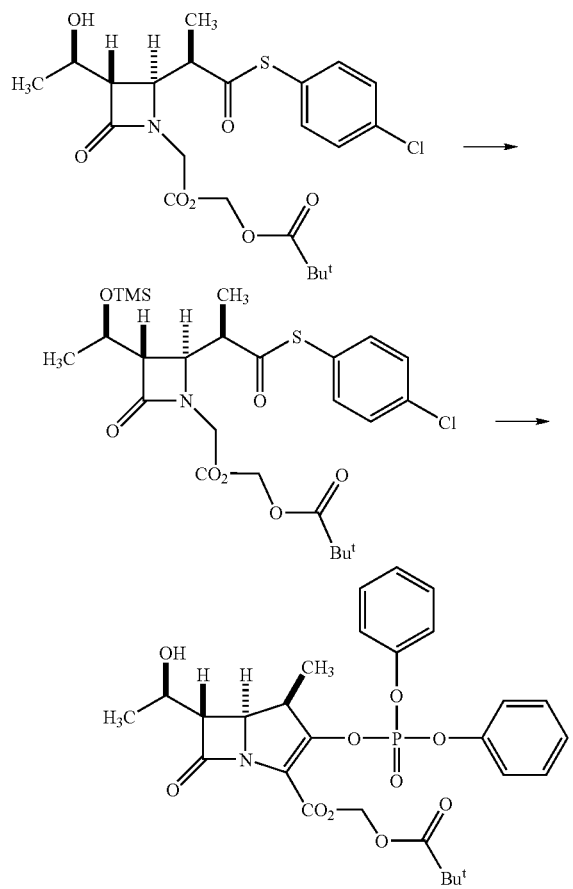

In 5 ml of toluene, was dissolved 0.97 g (2.0 mmol) of (3S,4S)-4-[(1R)-1-(p-chlorophenylthiocarbonyl)ethyl]-3-[(1R) -1-hydroxyethyl]-1-pivaloyloxymethyloxycarbonyl-methyl-2-azetidinone which was synthesized in the same manner as in Reference Example 1. To the resulting solution, was added 0.50 g. (5.0 mmol) of triethylamine and was dropwise added 0.39 g (3.6 mmol) of trimethylsilyl chloride at room temperature, followed by stirring the mixture for 15 hours at the same temperature. The reaction mixture was diluted with toluene. The toluene solution was washed with water several times. The resulting toluene solution was dried over sodium sulfate, and then the solvent was removed by evaporation.

To the resulting oily residue, was added 15 ml of a mixed solvent composed of tetrahydrofuran and toluene in a volume ratio of 1 to 2 to dissolve the oily residue. The solution was cooled to −25° C., and 0.475 g (4.2 mmol) of potassium tert-butoxide was added to the cooled solution, followed by stirring the mixture for one hour. Then, 0.30 g (2.1 mmol) of methyl iodide was added to the mixture at the same temperature. The resulting mixture was stirred for 20 minutes, followed by adding 0.60 g (2.2 mmol) of diphenylphosphoryl chloride to the mixture. The resulting mixture was stirred for 2.5 hours.

To the reaction mixture, were added ethyl acetate and water under cooling with ice. The mixed solution was adjusted to pH 3 with aqueous 1N hydrochloric acid. The ethyl acetate solution, which was obtained by phase separation, was washed with aqueous sodium bicarbonate solution and water, each several times. Then, the resulting solution was dried over sodium sulfate, and the solvent was removed by evaporation to obtain the title compound.

NMRδ (CDCl$_3$): 1.18-1.20 (12H, m), 1.29 (3H, d, J=4.9 Hz), 3.28 (1H, dd, J=2.4, 6.3 Hz), 3.45-3.51 (1H, m), 4.17-4.21 (2H, m), 5.77 (1H, d, J=5.5 Hz), 5.81 (1H, d, J=5.5 Hz), 7.21-7.40 (12H, m)

REFERENCE EXAMPLE 4

Production of (4R, 5R, 6S)-6-[(1R)-1-triethylsilyloxyetuyl]-3-diphenylpho sphoryloxy-4-methyl-7-oxo-1-azabicyclo[3.2.0]hept-2-ene-2 -carboxylic acid pivaloyloxymethyl ester

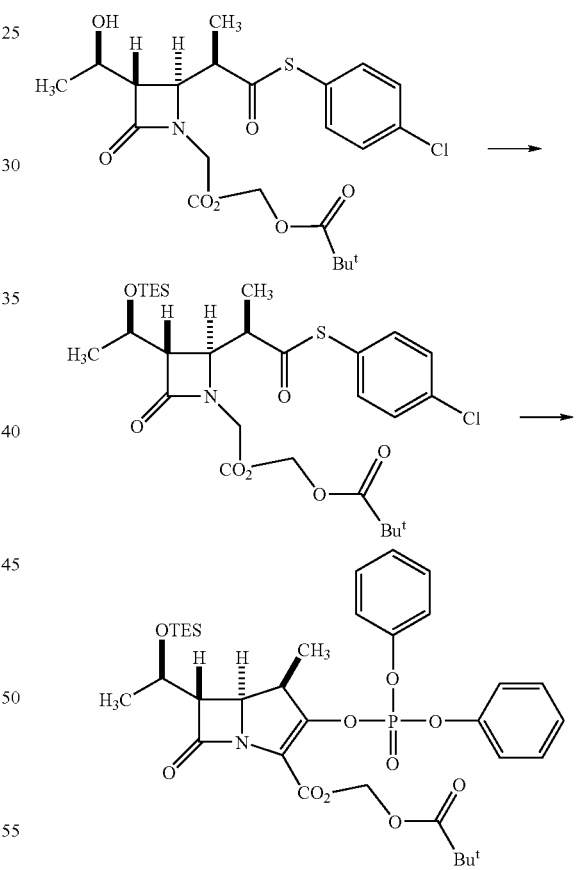

In 10 ml of toluene, was dissolved 0.493 g (1.0 mmol) of (3S, 4S)-4-[(1R)-1-(p-chlorophenylthiocarbonyl)ethyl]-3-[(1R)-1-hydroxyethyl]-1-pivaloyloxymethyloxycarbonyl-methyl-2-azetidinone which was synthesized in the same manner as in Reference Example 1. To the resulting solution, was added 0.17 g (1.7 mmol) of triethylamine and was dropwise added 0.24 g (1.6 mmol) of triethylsilyl chloride at room temperature, followed by stirring the mixture for 22 hours at the same temperature. The reaction mixture was diluted with 10 ml of toluene. The toluene solution was washed with water several times. The resulting toluene solution was dried over sodium sulfate, and then the solvent was removed by evaporation.

To the resulting oily residue, was added 6 ml of tetrahydrofuran to dissolve the oily residue. The solution was cooled to −25° C., and 0.232 g (2.1 mmol) of potassium tert-butoxide was added to the cooled solution, followed by stirring the mixture for 60 minutes. Then, 0.19 g (1.05 mmol) of benzyl bromide was added to the mixture at the same temperature. The resulting mixture was stirred for 20 minutes, followed by adding 0.30 g (1.1 mmol) of diphenylphosphoryl chloride to the mixture. The resulting mixture was stirred for 2 hours. The reaction mixture was diluted with 50 ml of toluene. The toluene solution was washed with 2.5% aqueous sodium bicarbonate solution and water, each several times under cooling with ice. The resulting toluene solution was dried over sodium sulfate, and then the solvent was removed by evaporation to obtain the title compound.

NMRδ (CDCl$_3$): 0.59-0.62 (6H, m), 0.94 (9H, t, J=8.1 Hz), 1.19-1.28 (15H, m), 3.23 (1H, dd, J=2.9, 6.6 Hz), 3.42-3.46 (1H, m), 4.13 (1H, dd, J=2.9, 10.3 Hz), 4.18-4.23 (1H, m), 5.78 (1H, d, J=5.5 Hz), 5.81 (1H, d, J=5.5 Hz), 7.15-7.43 (12H, m)

EXAMPLE 1

Production of pivaloyloxymethyl (1R, 5S, 6S)-2-[1-(1,3-thiazolin-2-yl)azet idin-3-yl]thio-6-[(1R)-1-hydroxyethyl]-1-methyl-carbapen-2-em-3-carboxylate

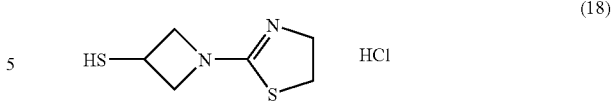

(18)

and was dropwise added 1.8 ml (10.3 mmol) of diisopropylethylamine under cooling with ice, followed by stirring the mixture for 1.9 hours at the same temperature. After the completion of the reaction, the solvent was removed by evaporation from the mixture, followed by adding 40 ml of ethyl acetate and 100 ml of water. The resulting solution was washed with aqueous potassium bicarbonate solution and aqueous sodium bicarbonate solution. To the resulting ethyl acetate solution, was added aqueous citric acid solution to make the solution acidic, thereby extracting the target compound into the water phase. It was extracted again into the ethyl acetate phase by adding 50 ml of ethyl acetate and potassium bicarbonate. The solvent was removed by evaporation from the solution until the weight of the solution is reduced to 12 g. To the resulting solution, was added 25 ml of heptane to precipitate a crystal, which was filtered and washed to obtain 1.87 g of a white crystal containing the title compound.

NMRδ (CDCl$_3$): 1.23 (9H, s), 1.23 (3H, d, J=7.1), 1.34 (3H, d, J=6.4 Hz), 3.13-3.21 (1H, m), 3.23 (1H, dd, J=2.7, 6.8

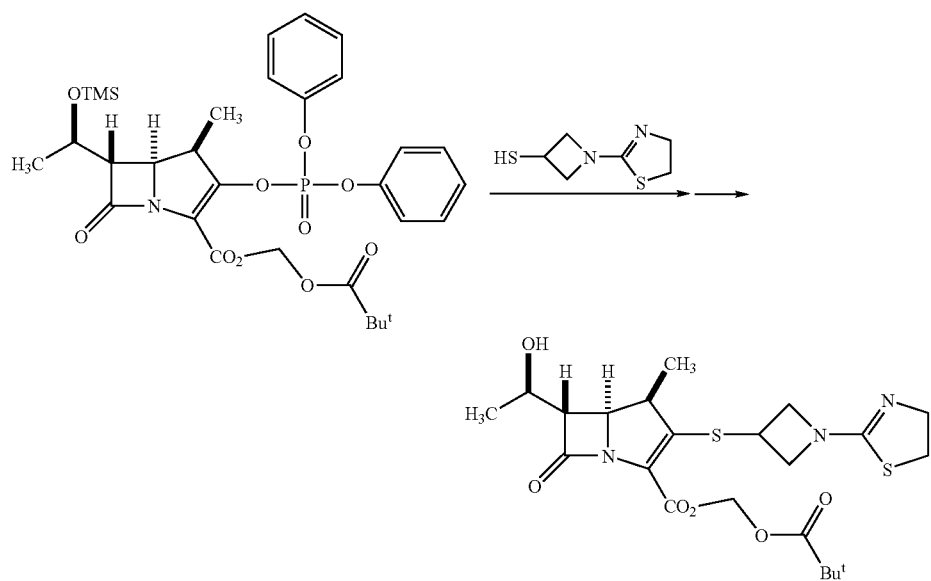

In 15 ml of acetonitrile, was dissolved 4.53 g of a yellow oily residue containing (4R, 5R, 6S)-6-[(1R)-1-trimethylsilyloxyethyl]-3-diphenylph osphoryloxy-4-methyl-7-oxo-1-azabicyclo[3.2.0]hept-2-ene-2-carboxylic acid pivaloyloxymethyl ester synthesized in Reference Example 2. To the resulting solution, was added 1.10 g (5.1 mmol) of a compound represented by formula (18):

Hz), 3.37 (2H, t, J=7.6 Hz), 3.94-4.03 (4H, m), 4.10-4.26 (3H, m), 4.36-4.42 (2H, m), 5.84 (1H, d, J=5.5 Hz), 5.97 (1H, d, J=5.5 Hz)

EXAMPLE 2

Production of pivaloyloxymethyl (1R, 5S, 6S)-2-[1-(1,3-thiazolin-2-yl)azet idin-3-yl]thio-6-[(1R)-1-hydroxyethyl]-1-methyl-carbapen-2-em-3-carboxylate

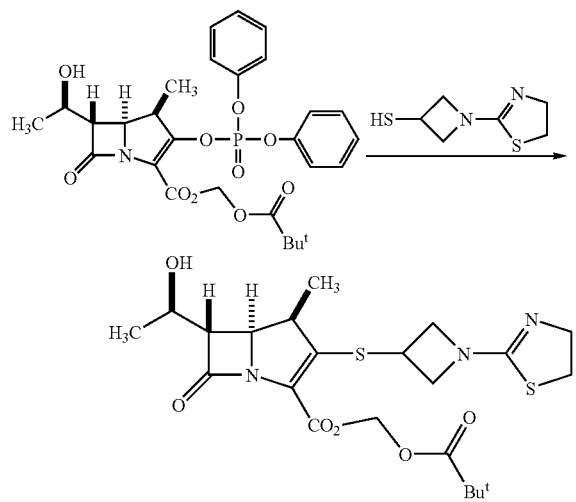

In 1 ml of acetonitrile, was dissolved 0.32 g of an oily residue containing (4R, 5R, 6S)-6-[(1R)-1-hydroxyethyl]-3-diphenylphosphoryloxy-4-methyl-7-oxo-1-azabicyclo[3.2.0]hept-2-ene-2-carboxylic acid pivaloyloxymethyl ester synthesized and purified in the same manner as in Reference Example 3. To the resulting solution, was added 0.07 g (0.33 mmol) of a compound represented by formula (18):

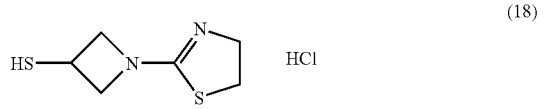

and was dropwise added 0.09 g (0.70 mmol) of diisopropylethylamine at −10° C., followed by stirring the mixture for 3 hours at the same temperature. After the completion of the reaction, 20 ml of ethyl acetate and 20 ml of water was added to the reaction mixture. To the resulting solution, was added aqueous citric acid solution to extract the target compound into the water phase. It was extracted again into the ethyl acetate phase by adding 20 ml of ethyl acetate and potassium bicarbonate. The resulting solution was dried over sodium sulfate, and then the solvent was removed by evaporation from the solution. The production of the title compound was confirmed by NMR analysis.

EXAMPLE 3

Production of pivaloyloxymethyl (1R, 5S, 6S)-2-[(3R)-5-oxopyrrolidin-3-yl]thio-6-[(1R)-1-hydroxyethyl]-1-methyl-carbapen-2-em-3-carboxylate

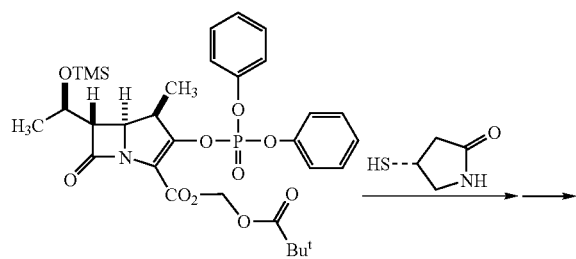

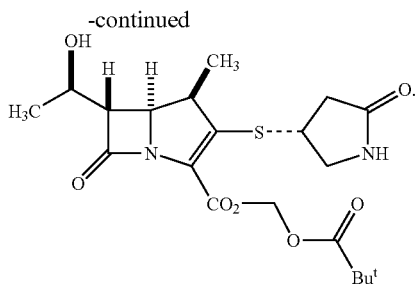

In 15 ml of acetonitrile, was dissolved 4.32 g of an oily residue containing (4R, 5R, 6S)-6-[(1R)-1-trimethylsilyloxyethyl]-3-diphenyiph osphoryloxy-4-methyl-7-oxo-1-azabicyclo[3.2.0]hept-2-ene-2-carboxylic acid pivaloyloxymethyl ester synthesized in the same manner as in Reference Example 2. To the resulting solution, was added 0.57 g (4.9 mmol) of a compound represented by formula (5):

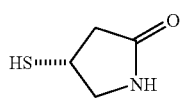

and was dropwise added 0.79 g (6.1 mmol) of diisopropylethylamine at 5° C., followed by stirring the mixture for 70 minutes at the same temperature. After the completion of the reaction, acetonitrile was removed by evaporation from the mixture, followed by dissolving the resulting mixture in 40 ml of ethyl acetate. The resulting solution was washed several times with aqueous sodium bicarbonate solution to remove the byproduced diphenylphosphate. To the resulting ethyl acetate solution, was added water and then aqueous 1N hydrochloric acid, until the solution has a pH of 3. The ethyl acetate solution, which was obtained by liquid separation operation, was washed with aqueous sodium bicarbonate solution and water, and then dried over sodium sulfate. The solvent in the resulting solution was removed by evaporation, and the residue was dissolved in 20 mL of acetone. To the resulting solution, was added 30 mL of toluene. Acetone was gradually removed by evaporation from the solution, and it was observed that the resulting solution became cloudy. The cloudy solution was stirred for one hour at a temperature in the range of 0 to 5°, and the resulting solution was filtered and washed to obtain a white crystal. The crystal was dissolved in acetone again. The resulting solution was subjected to the operations of toluene addition, removal of the solvent by evaporation, stirring, filtration and washing in the same manner as described above to obtain 0.70 g of a white crystal containing the title compound.

NMRδ (CDCl$_3$): 1.22 (9H, s), 1.27 (3H, d, J=7.1), 1.32 (3H, d, J=6.3 Hz), 2.39 (1H, dd, J=5.1, 17.1 Hz), 2.83 (1H, dd, J=8.1, 17.1 Hz), 3.26 (1H, dd, J=2.4, 6.8 Hz), 3.31-3.36 (1H, m), 3.84 (1H, dd, J=8.1, 10.7 Hz), 4.01-4.06 (1H, m), 4.22-4.28 (2H, m), 5.82 (1H, d, J=5.5 Hz), 5.96 (1H, d, J=5.5 Hz)

EXAMPLE 4

Production of pivaloyloxymethyl (1R, 5S, 6S)-2-[(3R)-5-oxopyrrolidin-3-yl]thio-6-[(1R)-1-hydroxyethyl]-1-methyl-carbapen-2-em-3-car boxylate

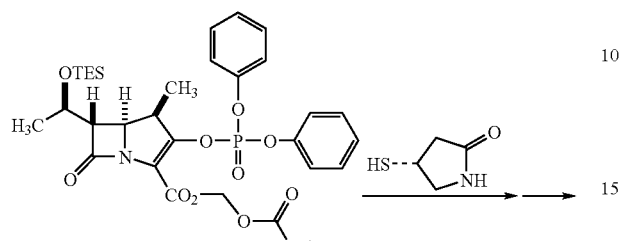

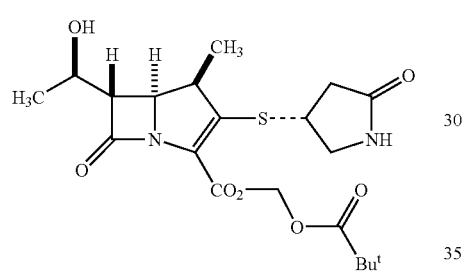

In 5 ml of acetonitrile, was dissolved 0.84 g of an oily residue containing (4R, 5R, 6S)-6-[(1R)-1-triethylsilyloxy-ethyl]-3-diphenylpho sphoryloxy-4-methyl-7-oxo-1-azabi-cyclo[3.2.0]hept-2-ene-2 -carboxylic acid pivaloyloxymethyl ester synthesized in the same manner as in Reference Example 4. To the resulting solution, was added 0.12 g (1.0 mmol) of a compound represented by formula (5):

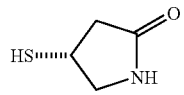

and was dropwise added 0.13 g (1.0 mmol) of diisopropyl-ethylamine at a temperature in the range of 0 to 5° C., followed by stirring the mixture for 3 hours at the same temperature. After the completion of the reaction, 20 ml of toluene and 20 ml of water were added to the reaction mixture, and then aqueous 1N hydrochloric acid was added to the resulting solution, until the solution has a pH of 2. The toluene solution, which was obtained by liquid separation operation, was washed with aqueous sodium bicarbonate solution and water, and then dried over sodium sulfate. The solvent in the resulting solution was removed by evaporation from the solution. The production of the title compound was confirmed by NMR analysis.

INDUSTRIAL APPLICABILITY

The present invention enables efficient and easy synthesis of various 1β-methylcarbapenem compounds for oral administration on which research and development have been actively conducted in recent years, and therefore, the present invention is industrially useful.

The invention claimed is:

1. A process for producing a compound represented by formula (2):

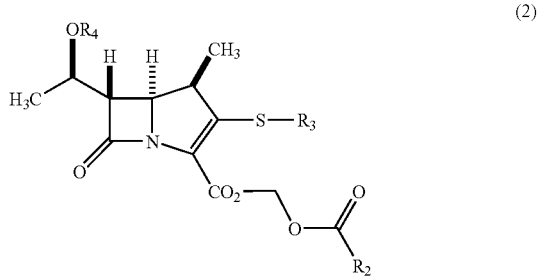

that comprises reacting a compound represented by formula (1):

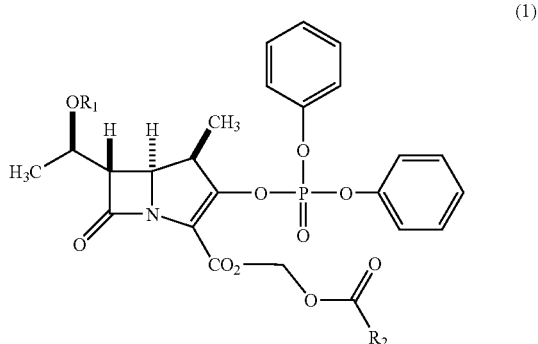

with a thiol compound represented by formula (3):

in the presence of a base and optionally eliminating protective group $R_1$:

where $R_1$ is a hydrogen atom, a trimethylsilyl group or a triethylsilyl group:

where $R_2$ is an alkyl group having 1 to 10 carbon atoms or a cycloalkyl group having 3 to 10 carbon atoms:

wherein $R_3$ is a thiol residue of a thiol compound represented by formula(4):

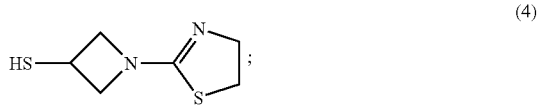

and wherein $R_4$ is a hydrogen atom, a trimethyisilyl group or a triethyisilyl group.

2. A process for producing a compound represented by formula (2):

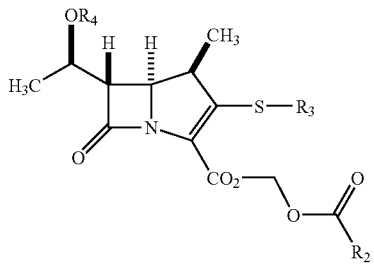
(2)

that comprises reacting a compound represented by formula (1):

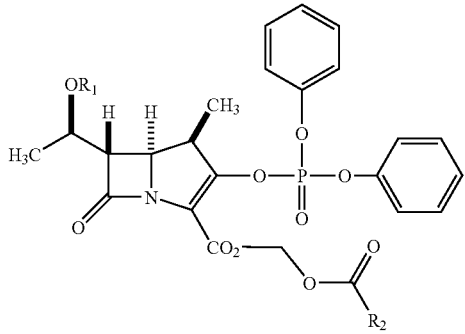
(1)

with a thiol compound represented by formula (3):

$$R_3-SH \quad (3)$$

in the presence of a base and optionally eliminating protective group $R_1$:

wherein $R_1$ is a hydrogen atom, a trimethylsilyl group or a triethylsilyl group:

wherein $R_2$ is an alkyl group having 1 to 10 carbon atoms or a cycloalkyl group having 3 to 10 carbon atoms;

wherein $R_3$ is a thiol residue of a thiol compound represented by formula (5):

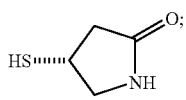
(5)

and wherein $R_4$ is a hydrogen atom, a trimethylsilyl group or a triethylsiyl group.

3. The process according to claim 1 or 2, wherein $R_2$ is a tert-butyl group.

* * * * *